United States Patent
Unfors

(10) Patent No.: US 7,313,223 B2
(45) Date of Patent: Dec. 25, 2007

(54) DEVICE, ARRANGEMENT AND METHOD FOR INDICATING POSITIONS ON AREAS EXPOSED TO X-RAY RADIATION SOURCES AND LIGHT SOURCES

(75) Inventor: Tomas Unfors, Billdal (SE)

(73) Assignee: Unfors Instruments AB, Billdal (SE)

( * ) Notice: Subject to any disclaimer, the term of this patent is extended or adjusted under 35 U.S.C. 154(b) by 0 days.

(21) Appl. No.: 11/415,990

(22) Filed: May 2, 2006

(65) Prior Publication Data
US 2006/0285646 A1 Dec. 21, 2006

Related U.S. Application Data

(63) Continuation of application No. PCT/SE2004/001539, filed on Oct. 25, 2004.

(30) Foreign Application Priority Data
Nov. 3, 2003 (SE) .................................... 0302885

(51) Int. Cl.
- H05G 1/64 (2006.01)
- G01T 1/24 (2006.01)
- A61B 6/08 (2006.01)

(52) U.S. Cl. .................. 378/98.8; 378/204; 378/205; 378/206; 250/336.1; 250/370.09; 250/370.1

(58) Field of Classification Search .............. 378/98.8, 378/162–164, 204–207; 250/336.1, 370.09, 250/370.1
See application file for complete search history.

(56) References Cited

U.S. PATENT DOCUMENTS 3,909,616 A * 9/1975 Redfield et al. ............ 378/147

(Continued)

FOREIGN PATENT DOCUMENTS

DE 3844716 C2 3/1989

(Continued)

OTHER PUBLICATIONS

Unfors Direct X-ray Ruler brochure.*

(Continued)

*Primary Examiner*—Allen C. Ho
(74) *Attorney, Agent, or Firm*—Schwegman, Lundberg & Woessner P.A.

(57) ABSTRACT

A unit (11) with a length (L) is utilized in a device for indicating the position of an edge (7a) of a first area (7) which is irradiated by an x-ray radiation source (2) in relation to an edge (9a) of a second area, completely or partially coinciding with the first area, which second area is illuminated by a light source. The unit is provided with a first and second parts separated by a mark (12), which parts are intended to extend inside the second area and outside the second area respectively. The unit (11) comprises x-ray radiation-indicating elements (14, 22) that assume a first indication state in the presence of x-ray radiation (6) and a second indication state in the absence of x-ray radiation. The position indication can be determined by means of the said mark and indication states. The invention also relates to an arrangement and a method for the said position indication. The unit can have small external dimensions, and constitutes a unit that is considerably simplified and easy to handle, while retaining a high degree of accuracy.

21 Claims, 3 Drawing Sheets

U.S. PATENT DOCUMENTS

Figure 1:
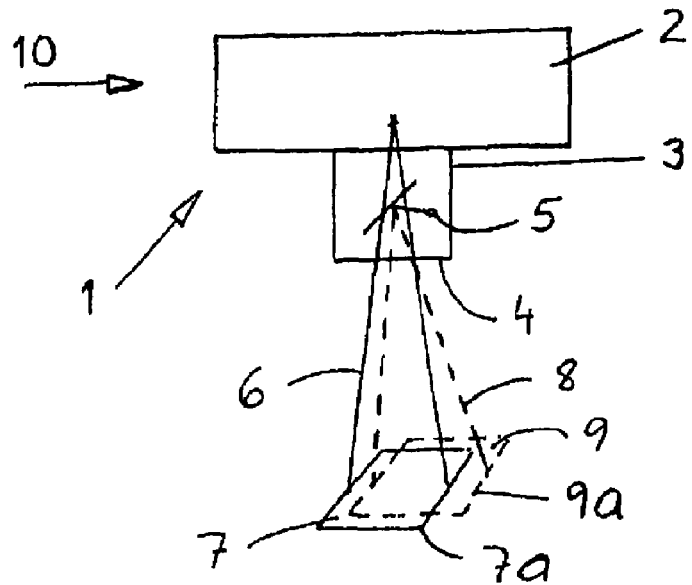

| | | | |
|---|---|---|---|
| 5,036,197 A * | 7/1991 | Voles | 250/332 |
| 5,039,867 A | 8/1991 | Nishihara | |
| 5,142,559 A | 8/1992 | Wielopolski et al. | |
| 5,710,428 A * | 1/1998 | Ko | 250/332 |
| 6,219,403 B1 | 4/2001 | Nishihara | |
| 6,260,999 B1 * | 7/2001 | Wofford et al. | 378/205 |
| 6,447,164 B1 * | 9/2002 | Polkus | 378/206 |
| 6,478,462 B2 * | 11/2002 | Polkus et al. | 378/207 |
| 6,590,958 B2 * | 7/2003 | Barber et al. | 378/98.8 |
| 6,626,569 B2 * | 9/2003 | Reinstein et al. | 378/206 |
| 7,176,467 B2 * | 2/2007 | Sandrik et al. | 250/370.11 |

FOREIGN PATENT DOCUMENTS

| | | |
|---|---|---|
| DE | 10143609 A1 | 3/2003 |
| WO | WO-8900703 A1 | 1/1989 |

OTHER PUBLICATIONS

"Written Opinion for Application No. PCT/SE2004/001539, date mailed Feb. 15, 2005", 3 pages.

Van Deer Meer, Frits, et al., "A new x-ray and light field superimposition detector", *Med. Phys.*, vol. 19, No. 3, (May/Jun. 1992), 587.

* cited by examiner

DEVICE, ARRANGEMENT AND METHOD FOR INDICATING POSITIONS ON AREAS EXPOSED TO X-RAY RADIATION SOURCES AND LIGHT SOURCES

RELATED APPLICATIONS

This application is a continuation under 35 U.S.C. 111(a) of PCT/SE2004/001539, filed Oct. 25, 2004 and published as WO 2005/043190 A1, on May 12, 2005, which claimed priority under 35 U.S.C. 119 to Sweden Application No. 0302885-9, filed Nov. 3, 2003, which applications and publication are incorporated herein by reference and made a part hereof.

The present invention relates, among other things, to a device for indicating the position of the edge of a first area illuminated by an x-ray radiation source in relation to the edge of a second area which is illuminated by a light source and which completely or partially coincides with the first area. The invention also relates to an arrangement and method for such indication.

The utilization of position detectors to determine whether x-ray radiation emitted from an x-ray radiation source coincides with radiation or light emitted from a utilized light source is already known. The latter is utilized as an aid for determining the area on a patient or object that is to be exposed to x-ray radiation. It is accordingly important that the x-ray radiation source and the light radiation source are coordinated so that the x-ray exposure is not carried out on an area that differs from the predetermined area. Such a deviation may mean that the x-ray procedure needs to be repeated and that the patient or object must be subjected to unnecessary exposure to the x-ray radiation source.

There is thus a pronounced need to be able to maintain an accurate coordination between the emitted x-ray radiation and the light illumination from the x-ray radiation-emitting equipment and the light-emitting equipment respectively, which comprise components, for example, in the form of x-ray tubes, lamps and/or fluorescent tubes, collimators/shutters, etc. The components can deteriorate and/or be subjected to external manual influences that cause changes in the emitting function of the x-ray radiation source or light source. There is thus a need to be able to check and adjust the equipment, in order to obtain the required accuracy in coordination when it is used on a patient or object. It is, in addition, important that checking and adjustment can be carried out using technically simple means which, in spite of their simplicity, must be able to work with the requisite reliability. There is also the requirement that the checking equipment in question should be able to be constructed with small external dimensions and should be easy to handle and easy and economical to manufacture.

The equipment or instruments known to date are relatively complicated and difficult to handle and have relatively large external dimensions. Thus, for the checking, the use is already known of markers and film developing, or arrangements utilizing fluorescent materials, which are time-consuming to use or require strong radiation, darkroom facilities, etc. The construction of indicating instruments utilizing electronics and fibre arrangements that connect x-ray radiation-sensitive components, diodes/sensors, etc, to the electronics, is already known. The fibres in the fibre arrangement must be arranged in a special way in order to be able to obtain correct functioning of the sensor or the sensor arrangement, which complicates the equipment.

The main object of the present invention is, among other things, to solve the abovementioned problems.

The principal characteristics of a device according to the invention are, among other things, that it comprises an elongated unit which is provided with first and second parts separated by a mark, which first and second parts are intended to extend inside the second area and outside the second area respectively. In addition, the unit comprises indicating elements that are sensitive to x-ray radiation and that are arranged to assume a first indication state, preferably an activated indication state, in the presence of x-ray radiation directed towards the element, and a second indication state, preferably an inactivated indication state, in the absence of x-ray radiation directed towards the element. The position indication is thereby able to be determined by means of the said mark and the indication states.

In further developments of the concept of the invention, the unit consists of an elongated or ruler-shaped unit that has at least one display that can be turned to face towards the x-ray radiation source. The display can be composed of elements arranged consecutively. Elements that are in positions within the first area mentioned in the introduction assume an activated indication state, and elements that are in positions outside the first area assume an inactivated indication state. The elongated or ruler-shaped unit can be provided with a sensor device that can act as an activation device or ON button. The unit can also be provided with a disconnection circuit that, after a predetermined period of time, disconnects predetermined indication states that have been assumed, after which time the reading can be considered to have been carried out. In additional embodiments, the device can be provided with automatically-starting reconnection circuits or reset circuits that can come into operation after the predetermined period of time. In a known way, the unit has an internal battery source and, in addition, is provided with a diode/sensor network, amplification network and logic network. The unit can consist of an elongated or tubular casing that has a flat lower outer surface. The casing can be arranged to contain a circuit board containing the components in question. The casing can also be designed with a slot that extends in the longitudinal direction and acts as a window, through which the elements can be viewed for determining the indication state. In an embodiment, the mark can consist of a mark located at the middle part of the casing, for example a red mark. Additional characteristics are apparent from the following subsidiary claims concerning the device in question.

The invention relates to an arrangement that can comprise two elongated units, the first unit of which is intended to extend inside the second area mentioned in the introduction and the second unit of which is intended to extend outside the second area. Both units comprise x-ray radiation-indicating elements that are arranged to assume a first indication state, preferably an activated indication state, in the presence of x-ray radiation, and a second indication state, preferably an inactivated indication state, in the absence of x-ray radiation. The position indication can be determined by means of the positions of the units and the indication states of the elements. In the arrangement, the end edges can be considered to act as a mark, for example a virtual mark, c.f. the mark described above.

The arrangement according to the invention can comprise one elongated unit arranged to be able to adopt two different positions, depending upon the application, where, in the first position, the unit extends from the second edge and inside the second area and, in the second position, the unit extends from the edge and outside the second area. As described above, the unit can comprise x-ray radiation-indicating elements which are arranged to assume a first indication state, preferably an activated indication state, in the presence of x-ray radiation, and a second indication state, preferably an inactivated indication state, in the absence of x-ray radiation. In this case, the position indication can be determined by means of the positions of the unit and the indication states of the elements and by the temporary disconnection of the x-ray radiation source between changes of the position of the unit. When the unit is applied in a direction from the edge of the light field where the x-ray radiation field extends beyond the light field or where the light field extends beyond the x-ray radiation field, the deviation can be determined by means of only one application of the unit.

A method according to the invention can be characterized in that the unit is applied to an edge of a light field area created by a light source, which unit comprises x-ray radiation-indicating elements, so that a first part that is separated by a mark from a second part is exposed to the light and the second part is positioned where it is not exposed to the light. An additional characteristic is that the x-ray radiation source is thereafter activated and the discrepancy is determined by reading off the activated and inactivated states of the x-ray radiation-indicating elements in the parts and the mark.

The method according to the invention can principally be characterized in that two units are applied to an edge of a light field area created by a light source, preferably edge to edge. As described above, the units comprise x-ray radiation-indicating elements. The application is carried out in such a way that one unit is exposed to the light and the other unit is positioned where it is unexposed to the light. The x-ray radiation source can thereafter be activated and the discrepancy can be determined by means of the activated and inactivated states of the x-ray radiation-indicating elements.

By means of what is proposed in the above, an exceedingly simple unit and an exceedingly simple method for the use of the unit are obtained. Thus, for example, in a first stage, the unit or ruler can be placed with its centre at the edge of the light. Thereafter the unit or ruler is exposed to x-ray radiation. The elements that receive the x-ray radiation are switched on or activated. Elements can be arranged with a light column function where the elements are switched on accordingly (as in a speedometer). The unit itself is activated automatically when the x-ray radiation incides on any one of its ends for a certain period of time. The criterion for activation of the elements or the light column function can be arranged in various ways and using various parameters. The unit can be switched on and off in a relatively simple way. The unit can consist of a unit with a mark, for example on its middle part. Alternatively, the unit can consist of two interacting parts, which parts are laid end to end, with the edge contact being regarded as a mark. The unit can also consist of one unit that is moved during the interval between two activations of the x-ray radiation source when carrying out the checking procedure. During one activation, the unit is applied in such a way that it extends from the edge and into the light field, while, in the second position, it extends from the edge and outwards from the light field. The unit and the arrangement can also operate with several units in order to determine the discrepancy between several edges of the light field and the x-ray radiation field. Alternatively, the same unit or units can be used at the different edges during different activations of the x-ray radiation source.

Figure 2:
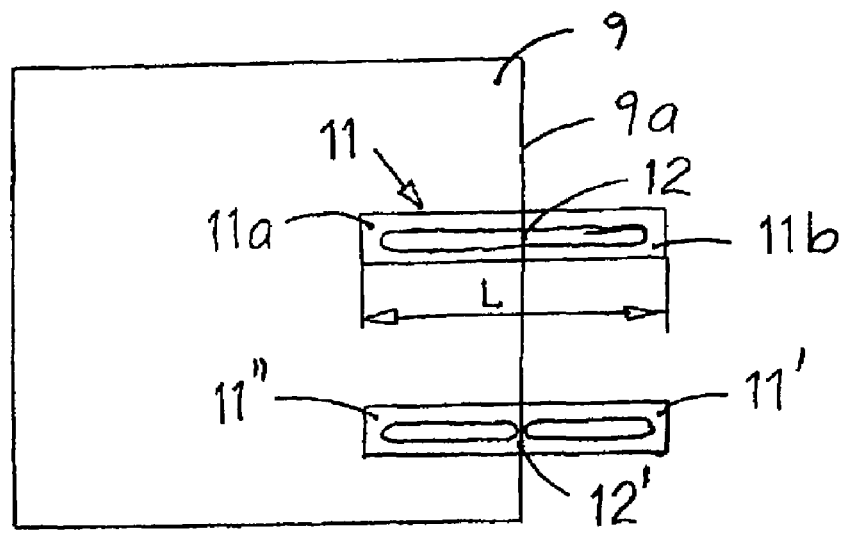
Figure 3:
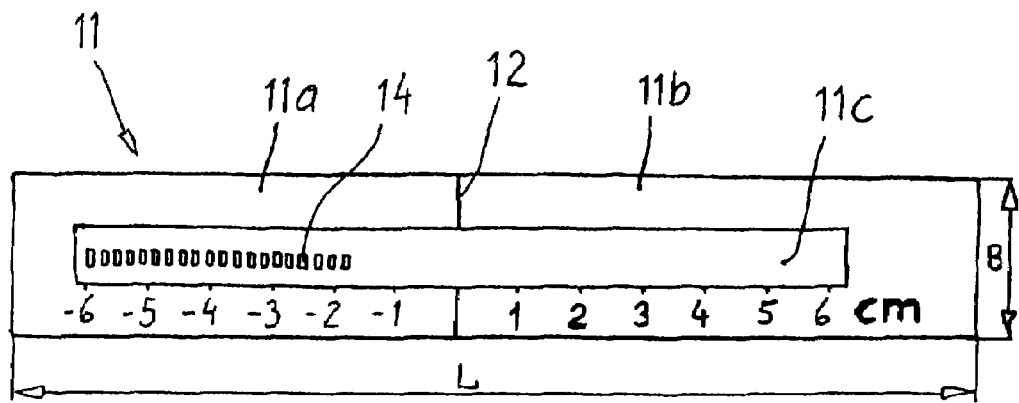
Figure 4:
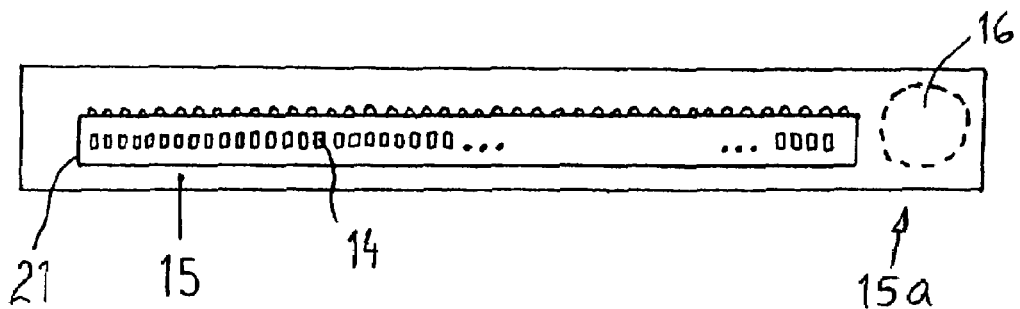
Figure 5:
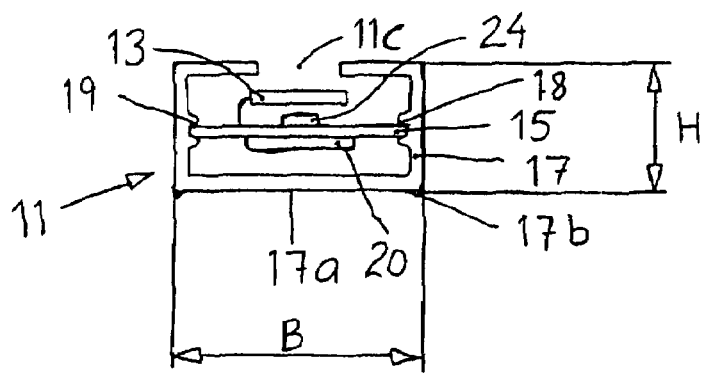
Figure 6:
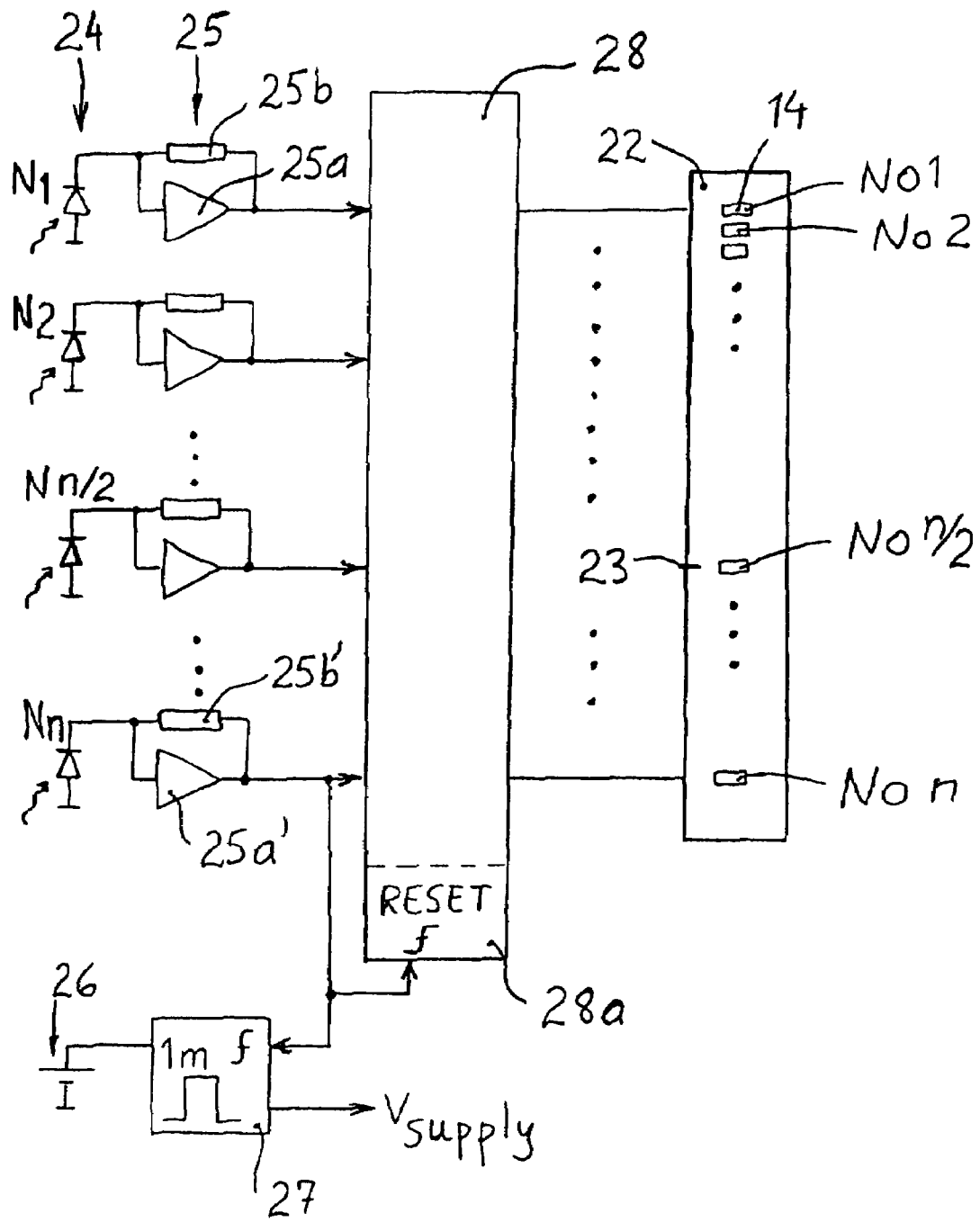

A currently-proposed embodiment of the device, arrangement and method according to the invention will be described below with reference to the attached drawings in which FIG. 1 shows in perspective and in outline the illumination of first and second areas by means of an x-ray radiation source and a light source arranged in a piece of equipment with x-ray tube, collimator/shutter and light source, FIG. 2 shows in perspective from above and in outline the application of the device or the unit on an edge of a light field area, with a first and a second example being shown with a combined or single unit and divided or interacting units respectively, FIG. 3 shows the unit from above, FIG. 4 shows a circuit board comprised in the unit according to FIG. 3 from one long side, FIG. 5 shows in cross-section the construction of the unit, enlarged in relation to FIGS. 3 and 4, and FIG. 6 shows in outline, schematically and expanded, the construction of a diode/sensor network, amplification network and logic network arranged in association with indication elements that can assume different indication states.

In FIG. 1, equipment that can be utilized, for example, in a hospital is indicated by 1. The equipment comprises in a known way an x-ray tube 2, a collimator/shutter housing 3 and a collimator/shutter 4. A light source is indicated by 5. The x-ray tube, which thus constitutes an x-ray radiation source in accordance with the above, gives rise when it is activated to an x-ray radiation which is symbolized by 6. The x-ray radiation incides on an area 7, here designated the first area. The light source 5 gives rise in a corresponding way to a light emission 8 which incides on an area 9, here designated the second area. In accordance with FIG. 1, there can be a discrepancy between the areas 7 and 9, that is the areas can be displaced in relation to each other. It is therefore important that an indication can be made of the size of the discrepancy, so that it is possible to adjust or replace the various components 2-5 in a known way. This type of adjusting and service work can be carried out on the equipment 1 in a known way and will therefore not be described in greater detail here. The light field area 9 has an edge or a partial perimeter 9a. In a corresponding way, the area 7 has an edge or a partial perimeter 7a. In accordance with the concept of the invention, a measurement is carried out of the discrepancy between the said edge 9a and the edge 7a. In order to obtain indications of the deviation around the whole of the perimeter of the light field area, according to the embodiment, indication measurements are carried out on two or more edges or partial perimeters. In the event of a discrepancy of a relevant size being determined, an adjustment is then carried out following the measurement of several edges or partial perimeters. In FIG. 1, an activating function for the connection and disconnection (switching on and switching off) of the x-ray tube 2 is indicated symbolically by 10.

In FIG. 2, an indication unit is represented by 11. The unit 11 has a length L and the unit can be considered to be divided into or consist of two parts 11a and 11b. In addition, in the embodiment shown, the unit is provided with a mark 12 in the form of a line, which extends in the transverse direction of the unit. The mark can consist of a red mark. In the present case, the mark separates or marks the first and the second parts 11a and 11b. In accordance with the concept of the invention, the unit is to be positioned at the edge 9a of the light field 9 in such a way that the mark coincides with the edge in question. In this way, the first part will extend from the edge 9a and into the light field and the second part will extend from the edge and away from the light field. In FIG. 2, a second embodiment of the unit arrangement is also shown. In this case, the unit arrangement can consist of two separate parts 11' and 11", with the part 11' corresponding to the part 11b and the part 11" corresponding to the part 11a. In an embodiment, the parts can be placed together via their end edges which, in FIG. 2, are symbolized by 12', which end edges can thus be considered to constitute or correspond to the said mark 12 in the case of a single unit. In an additional alternative, the unit can consist only of the unit part 11' which is moved between the positions shown for 11' and for 11" during the interval between two different activations of the x-ray radiation source, c.f. the symbolically-indicated switching-on and switching-off function 10 in FIG. 1.

FIGS. 3, 4 and 5 show the construction of an embodiment of the new unit. In these figures, the unit 11 is the shape of a ruler 13 and has a length L that can be between 50-150 mm and can preferably be approximately 100 mm. The unit has a slot 11c extending in its longitudinal direction, through which the elements 14 can be viewed. The elements can assume two different indication states, namely activated and inactivated indication states. In the present case, the elements which are arranged in the first part 11a are shown in an activated state, while the elements arranged in the part 11b are shown in an inactivated state. The elements can interact with sensors that are sensitive to x-ray radiation and that are described below (c.f. 24 in FIG. 6), and when the x-ray radiation incides on the sensors, the elements assume their activated state, which preferably consists of a switched-on state. The elements are arranged or mounted on a circuit board 15 together with the sensors and components described below. The unit has a height H of 10-15 mm and a width B of 20-25 mm.

In accordance with FIG. 4, a battery 16 in the form of a long-life battery is arranged at one end 15a of the circuit board. Examples of types of battery are known lithium button cell batteries.

FIG. 5 shows that the unit has a tubular casing with an essentially rectangular cross section. The casing is indicated by 17 and its external lower surface is indicated by 17a. The circuit board 15 is supported inside the casing which, for this purpose, is provided with grooves 18, 19 into which the circuit board can be inserted from one end of the unit. On its upper surface, the circuit board has a display with LCD elements with underlying x-ray-sensitive sensors (c.f. FIG. 6) (LCD=Liquid Crystal Display). On its undersurface, the circuit board 15 has amplifier circuits and/or logic circuits 20. The outside of the casing is provided with longitudinal furrows or ridges 17b.

The LCD elements are arranged consecutively in an arrangement that can be likened to a light column function. In the example shown, the number of elements and the number of sensors can be 40 or more. The width of the light column can be, for example, 2.5 mm. In an embodiment, the sensors can comprise or consist of silicon diodes. In the embodiment, the x-ray radiation switches on a number of LCD elements which, in this case, corresponds to the irradiation of a corresponding number of sensors by the x-ray radiation source. In the said light column function, the activated or switched-on part of the light column increases in length the further into the irradiated x-ray field the unit is placed. In an embodiment, a criterion for activating the elements is utilized, where an underlying or preceding element has a signal level significantly larger than a subsequent element. By "significantly" can be meant here signal levels that are 50% larger than the signal level for the preceding element. Alternatively, all elements that have a signal level within 50% (or within the range 40-60%) of the maximum signal level can be switched on. At one end, the unit is provided with a sensor 21 that acts as an ON button in the event of irradiation.

In FIG. 6, the LCD elements that form a display are indicated by 22. The display comprises a number of elements indicated by No1, No2-Non/2 and Non. The measurement line of the unit or the measuring ruler is represented by 23 and corresponds to the element Non/2 in the display 22. Below each display element, that is the display elements No1 to Non, there is a corresponding x-ray-sensitive element, with the x-ray-sensitive elements being symbolized by 24 in FIG. 6. These x-ray-sensitive elements are indicated by N1, N2 . . . Nn/2 . . . Nn. In an embodiment, the end of the display with the Non$^{th}$ element is to be positioned so that it is pointing inwards into the light field. In the event of an x-ray exposure, the x-ray radiation incides on certain of the x-ray sensors 24. The x-ray sensors 24 convert the x-ray intensity to a proportional current which is converted to a voltage. This is carried out in a known way and will therefore not be described in greater detail here. Pre-amplifiers (differential amplifiers) which are symbolized by 25 are arranged after the x-ray-sensitive elements 24. The pre-amplifiers consist of current-to-voltage transducers. As the current from the x-ray-sensitive elements 24 is of the order of fractions of nA to a number of µA, pre-amplifiers are used that work with high amplification levels and high feedback resistance and are therefore arranged with high resistance, for example resistance of 1-10 Mohm.

In FIG. 6, a pre-amplifier 25 is indicated by op-amp or differential amplifier 25a and a resistance by 25b. The pre-amplifier (25a', 25b') for the element Nn has a continuous power supply from a battery 26 and, in the event of an x-ray exposure, it can trigger or start up a unit 27 to supply power to all parts and components in the unit (11 in FIG. 2). In order to save battery power, the power supply is switched off after the unit has been activated for approximately one minute (or within the range 0.5-2 minutes), which gives the user time to read off the display 22. The pre-amplifier (25a', 25b') also starts up or triggers a logic unit 28 so that all the display elements in 22 are inactivated or switched off when a new x-ray exposure is generated. The logic unit 28 compares the signals from the pre-amplifiers 25 and chooses to activate or switch on corresponding display elements which fulfill the criterion of signal $x \geq 50\% \times \text{signal}_{x-1}$, and all elements X to n. The unit thus works with an automatic reset function that is initiated in the event of each new exposure to x-ray radiation. In the figure, the reset function is indicated by 28a. The respective x-ray-sensitive elements 24 with associated LCD segments or LCD elements are positioned in essentially the same place on the circuit board. It is, of course, possible to utilize components that comprise the x-ray-sensitive element and the LCD segment integrated together. The parts comprised in the unit can be constructed in a known way. The discrepancy can be determined by determining which of the consecutively-arranged elements up to the edge of the x-ray field are switched on and by measuring or determining the distance from the outermost switched-on element to the mark that is placed at the relevant edge or partial perimeter of the light field.

The invention is not limited to the embodiments shown above as examples, but can be modified within the framework of the following patent claims and concept of the invention.

The invention claimed is:

1. An X-ray indicating unit, comprising:
   a support;
   a plurality of X-ray sensors distributed over a portion of the support to form a consecutive arrangement of sensors, wherein the plurality of X-ray sensors being positionable relative to an X-ray device radiation field,
   a plurality of indicating elements, each of which being capable of assuming two different states: an activated state and an inactivated state based on sensed X-rays, wherein the plurality of indicating elements form a display for displaying a current state of each indicating element, each indicating element being associated with a corresponding X-ray sensor such that the indicating element and the X-ray sensor in each element-sensor pair are electronically connected to each other and positioned in essentially a same place of the support,
   said element-sensor pair being arranged such that a signal from the X-ray sensor is capable of activating its corresponding indicating element.

2. The X-ray indicating unit according to claim 1, wherein the element-sensor pair comprises electronic means for allowing the sensors to activate the indicating elements.

3. The X-ray indicating unit according to claim 1, wherein the support comprises an elongated casing with a substantially flat external lower surface, said sensors and indicating elements being distributed in a longitudinal direction of the casing.

4. The X-ray indicating unit according to claim 1, wherein the support includes a circuit board on which the sensors and the indicating elements are arranged.

5. The X-ray indicating unit of claim 4, wherein the circuit board supports electronic components connecting the sensors and the indicating elements.

6. The X-ray indicating unit according to claim 5, wherein the indicating elements are liquid crystal display elements.

7. The X-ray indicating unit according to claim 6, wherein the sensors comprises silicon.

8. The X-ray indicating unit according to claim 1, wherein the sensors comprises silicon.

9. The X-ray indicating unit according to claim 1, wherein the indicating elements are liquid crystal display elements.

10. The X-ray indicating unit according to claim 1, wherein the support includes a first part to be positioned within a light field and a second part to be positioned outside the light field, and wherein the element-sensor pairs to indicate position of an X-ray field relative to the light field.

11. The X-ray indicating unit of claim 1, wherein the support includes a sensor arranged at an end of the support, and wherein the sensor to activate element-sensor pairs with the sensor being exposed to x-ray radiation.

12. The X-ray indicating unit of claim 11, wherein the support includes a disconnection circuit cancelling the first indication state and functioning a predetermined period of time, during which the position determination is carried out.

13. The X-ray indicating unit of claim 12, wherein the disconnection circuit operates with a predetermined period of time of 0.5-2.0 minutes.

14. The X-ray indicating unit of claim 12, wherein the support includes an automatically-starting reconnection circuit that functions when a new exposure commences that is followed by a completed exposure to x-ray radiation.

15. The X-ray indicating unit of claim 1, wherein the support includes an internal battery source, a sensor network, an amplification network and a logic network, the sensors being arranged to operate with current between fractions of nA and several μA with a distance between light field and the x-ray field generating equipment and light and X-ray areas is approximately one meter.

16. The X-ray indicating unit of claim 15, wherein the logic network includes a connection function and a disconnection function for the indicating elements.

17. An X-ray positional indicator to determine the relative positions of an alignment area and an X-ray area, comprising:
   a unit including an elongate first part and an elongate second part, the first part to extend into inside the alignment area and not outside the alignment area, the second part to extend outside the alignment area and not inside the alignment area;
   a first plurality of X-ray sensor and indicating element pairs linearly arranged on the first part, the first plurality of pairs being distributed on the first part to form a consecutive arrangement of pairs, the X-ray sensor and indicating element of each of the first plurality of pairs being positioned at essentially a same location on the first part, wherein the first plurality of pairs to sense an X-ray emission and indicate where an X-ray emission is received at the X-ray area if and where an X-ray emission is received outside the alignment area;
   a second plurality of X-ray sensor and indicating element pairs linearly arranged on the second part, the second plurality of pairs being distributed on the second part to form a consecutive arrangement of pairs, the X-ray sensor and indicating element of each of the second plurality of pairs being positioned at essentially a same location on the second part, wherein the second plurality of pairs to sense an X-ray emission and indicate if and where an X-ray emission is received outside the alignment area;
   wherein the indicating elements of both the first plurality of pairs and the second plurality of pairs include an activated state based on a presence of sensed X-rays by the corresponding sensors and an inactivated state based on a lack of sensed X-rays by the corresponding sensors;
   a first electrical connection for the X-ray sensor and the indicating element of each first pair; and
   a second electrical connection for the X-ray sensor and the indicating element of each second pair.

18. The X-ray positional indicator of claim 17, wherein the indicating elements of both the first plurality of pairs and the second plurality of pairs include visual indicators, wherein the X-ray sensors of both the first plurality of pairs and the second plurality of pairs include diodes, and wherein the first electrical connection and the second electrical connection each include a differential amplifier.

19. The X-ray positional indicator of claim 17, wherein activated ones of the indicating elements of both the first plurality of pairs and the second plurality of pairs remain activated for at least 0.5 minute to allow a user to enter an X-ray room and read the indicating elements.

20. Method for indicating a discrepancy between outgoing radiation from x-ray radiation and light radiation sources that illuminate at least one area, comprises:
   applying a unit to an edge or partial perimeter of a light field area created by the light source with a first part of the unit exposed to the light radiation and a second part of the unit positioned where it is not exposed to the light radiation;
   activating the x-ray radiation source;
   sensing the x-ray radiation;
   activating x-ray radiation-indicating elements based on the sensed x-ray radiation; and determining a relative position of x-ray radiation to light radiation by reading off activated and inactivated states of the x-ray radiation-indicating elements and a mark.

21. The method of claim 20, wherein applying a unit includes applying a further unit to an edge of light field area created by the light source with a third part exposed to the light and a fourth part positioned where it is not exposed to the light.

* * * * *